United States Patent
Shikakubo et al.

[11] Patent Number: 5,943,759
[45] Date of Patent: Aug. 31, 1999

[54] METHOD FOR MANUFACTURING NEEDLE ATTACHED SUTURES AND APPARATUS THEREFOR

[75] Inventors: Kenji Shikakubo, Sakaimachi; Satoshi Omuraya, Satte; Gennai Yanagisawa, Matsumoto, all of Japan

[73] Assignee: Kabushiki Kaisha Azwell (Azwell Inc.), Osaka, Japan

[21] Appl. No.: 08/930,446

[22] PCT Filed: Jan. 29, 1997

[86] PCT No.: PCT/JP97/00199

§ 371 Date: Sep. 29, 1997

§ 102(e) Date: Sep. 29, 1997

[87] PCT Pub. No.: WO97/27806

PCT Pub. Date: Aug. 7, 1997

[30] Foreign Application Priority Data

Feb. 2, 1996 [JP] Japan ..................................... 8-017630

[51] Int. Cl.[6] .................................................. B21D 39/00
[52] U.S. Cl. ................................ 29/517; 29/515; 29/785; 29/788; 163/5
[58] Field of Search .............................. 29/515, 788, 517, 29/712, 785; 606/223, 224, 225; 163/1, 5

[56] References Cited

U.S. PATENT DOCUMENTS 4,922,904  5/1990  Uetake et al. .
5,495,420  2/1996  Demarest et al. ...................... 364/468

FOREIGN PATENT DOCUMENTS 63-212027  9/1988  Japan .
63-212028  9/1988  Japan .
257243  2/1990  Japan .
5237124  9/1993  Japan .

Primary Examiner—P. W. Echols
Assistant Examiner—John Hong
Attorney, Agent, or Firm—Jordan and Hamburg LLP

[57] ABSTRACT

This invention relates to a method for manufacturing a needle attached suture and an apparatus therefor. A needle attached suture is obtained by inserting a suture into an insertion hole formed in the end of a needle N which is held by a needle retaining unit 16 and by swaging the end of the needle with the suture. The method and the apparatus have been developed to accurately position the end of the needle for swaging with the suture to stabilize the swaging strength between the suture and the needle. Before the swaging, the needle is held by the needle retaining unit 16, and the end of the needle N is pushed to a certain position by a rod 99 or its equivalent. Thereby, the end of the needle N relative to the needle retaining unit 16 is accurately positioned.

12 Claims, 11 Drawing Sheets

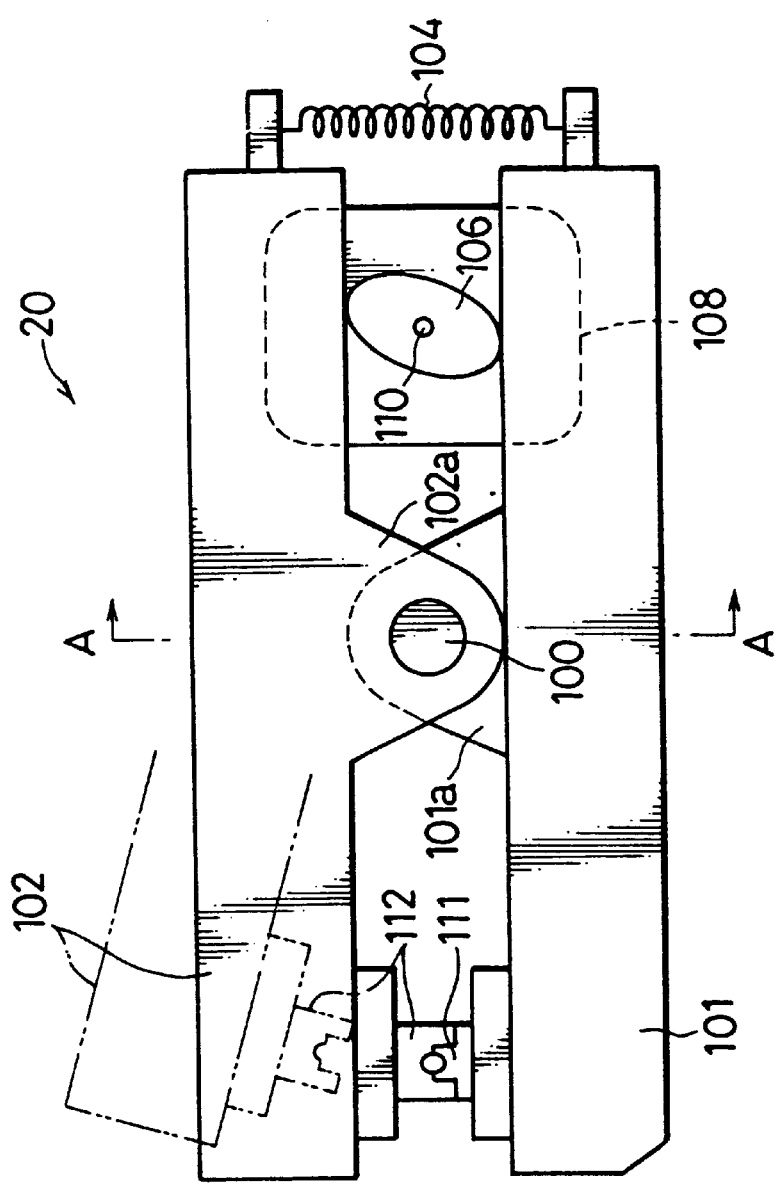
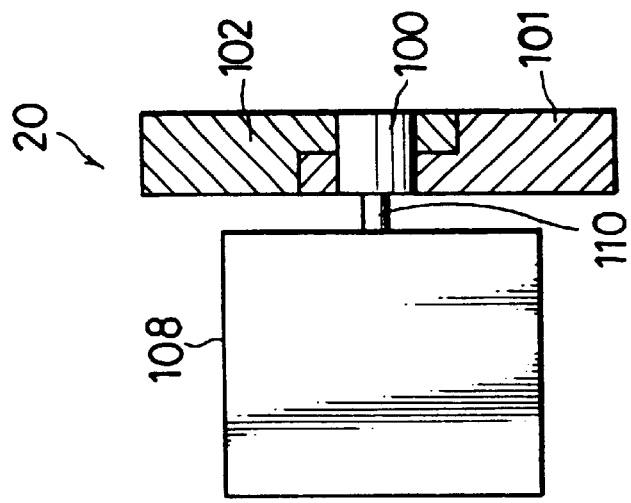
FIG. 12A
FIG. 12B

METHOD FOR MANUFACTURING NEEDLE ATTACHED SUTURES AND APPARATUS THEREFOR

BACKGROUND ART

This invention relates to a method for manufacturing needle attached sutures and an apparatus therefor, in which the end of a needle used for surgical operations and the like is swaged in a state that the lead end of a suture is inserted in an insertion hole formed in the end of the needle to combine the needle with the suture together.

Recently, in the field of medical industry, there have been marketed sterilized needle attached sutures for surgical operations in which the lead end of a suture is fixedly attached to a needle. There have generally been known apparatuses for manufacturing such needle attached sutures comprising a needle retaining unit for retaining a needle in a certain direction, and a swaging device for fixedly swaging the end of the needle with the lead end of a suture inserted in an insertion hole formed in the end (disclosed in, e.g., Japanese Examined Patent Publication No. HEI 4-66579).

The prior art apparatus mentioned above has been involved with the following problems to overcome.

In producing such needle attached sutures, a strength for combining the end of a needle with a suture (swaging strength) is an essential matter for the following reasons. If the swaging strength is too small, it is highly likely that merely applying a relatively small tension force during a surgical operation would result in loosening out of the suture from the end of the needle. On the other hand, if the swaging strength is excessively large, there should be considered the case where the suture cannot be pulled out of the needle when a person tries to detach the needle from the suture with fingers or a needle holder after a suturing operation is completed.

In order to eliminate the above drawbacks, the swaging strength is necessary to be set within a predetermined allowable range. However, to obtain a swaging strength of a desired value, it is important to accurately position the end of the needle during a swaging step to a target position (i.e., to exactly adjust a position at which the end of the needle is swaged by the swaging device to a predetermined position).

A high technique is required to set every needle exactly in the same direction at the same position relative to the needle retaining unit. Even if the needle is directed in the correct direction before setting the needle on the needle retaining unit, the position of the needle may be displaced during an actual setting. Therefore, it is highly likely that the actual position of the end of the needle after setting may be displaced from the target setting position. This positional displacement results in producing needle attached sutures with the swaging strength varied greatly.

In view of the above, this invention is directed to a method for manufacturing needle attached sutures and an apparatus therefor, capable of precisely positioning the end of a needle held by a needle retaining unit at a predetermined position to stably obtain a desired swaging strength.

DISCLOSURE OF THE INVENTION

To solve the above problems, this invention has adopted the following arrangement.

This invention is directed to a method for manufacturing a needle attached suture in which a suture is combined with a needle by swaging an end of the needle with the suture being inserted in an insertion hole formed in the end, while retaining the needle with the end thereof exposed outside, the method comprising the steps of: (a) retaining the needle in such a manner that the needle is displaceable in a direction along an axis of the end thereof; (b) positioning the end of the needle by pushing the end; and (c) swaging the end of the needle with the suture.

As an apparatus for executing the above method, the following arrangement is desirable. Specifically, the apparatus for manufacturing needle attached sutures comprises: needle retaining means for retaining a needle with an end thereof exposed outside such that the needle retained by the needle retaining means is displaceable in a direction along an axis of the end of the needle; swaging means for swaging the end of the needle with a suture being inserted in an insertion hole formed in the end to combine the suture with the needle; and pushing means for pushing the end of the needle to a predetermined target position relative to the needle retaining means to render the end position of the needle coincident with the target position.

According to the above method and apparatus, the needle is first retained by the needle retaining means, and then, before the end of the needle is swaged, the end thereof is pushed by the pushing means. Accordingly, the end of the needle relative to the needle retaining means is assuredly positioned with high precision. Thereby, a swaging strength (combining strength between the needle and the suture) obtained by the swaging step after the pushing step is stabilized.

In the above apparatus, the needle retaining means may be fixedly mounted at a certain position, and the pushing means and the swaging means may be selectively transported to the needle retaining means. In this case, however, the arrangement is required in which both the pushing means and the swaging means are transportable, and thus a facility for transportation of a large scale is required. In addition to this, positioning of the pushing means and the swaging means is difficult.

Contrary to the above altered arrangement, preferably, the apparatus may have transport means for transporting the needle retaining means, from a position at which the end of the needle is pushed by the pushing means to such a position as to allow the end thereof to be swaged by the swaging means, while providing the pushing means at a position different from the swaging means. With this arrangement, merely moving the needle retaining means of a relatively small size attains smooth transportation of the needle from the pushing step to the swaging step.

As well as a belt conveyor and a transportable pickup device, preferably, the transport means may include a turntable operable to rotate, and the turntable may be arranged with a plural needle retaining means along an outer circumference thereof. Thereby, efficient production of needle attached sutures can be realized because the needle retaining means can be operated efficiently.

Preferably, the apparatus may further comprise gripping means arranged between the needle retaining means and the pushing means for restricting a certain end portion of the needle except a rearmost end thereof from moving in a direction different from the pushing direction of the pushing means. Thereby, there can be eliminated the possibility that the needle is deflected in a direction other than the pushing direction when being pushed by the pushing means. Accordingly, a proper needle swaging step can be executed.

Preferably, the gripping means may include a gripping plate for gripping the end of the needle, and the pushing means may push the end of the needle to such a position as to render the pushing means in contact with a surface of the gripping plate opposing to the pushing means. With this arrangement, the end of the needle can be positioned accurately to the target position i.e., in flush with the surface of the gripping plate.

More preferably, the needle retaining means may include a retainer main body carried by the transport means, an openable member linked to the retainer main body to be openable with respect to the retainer main body, and drive means for setting the openable member to an opened state and a closed state, the needle being held by the retainer main body and the openable member in the closed state. With this arrangement, a needle setting on the retainer main body is facilitated because the openable member is set to an opened state. Shifting of the openable member from the opened state to a closed state attains assured holding of the needle by the needle retaining means.

The pushing means in this invention is not limited to any specific arrangement. Preferably, the pushing means may include an expandable member, and the expandable member may be so arranged as to cause a lead end thereof to push the end of the needle to a predetermined position when the expandable member is set to an expanded state. With this arrangement, setting the moving stroke of the expandable member at a desired value enables accurate positioning of the end thereof at which the needle is to be pushed.

According to this invention., it is required to set the needle in a correct direction and position on the needle retaining means. In order to comply with this requirement, preferably for setting automatically, the apparatus may further comprise needle orientation adjuster means for rendering an orientation (direction and position) of the needle coincident with a predetermined target orientation, and needle transport means for transporting the needle in the orientation thereof adjusted by the needle orientation adjuster means to the needle retaining means.

More preferably, the needle orientation adjuster means may include an adjuster table horizontally movable and rotatable about an axis thereof for placing the needle thereon, table drive means for moving the adjuster table to a desired direction, image recognizing means for recognizing an image of the needle placed on the adjuster table, and drive control means for controlling the table drive means to render a position of the image recognized by the image recognizing means coincident with a stored target image position.

With this arrangement, comparison between the image recognized by the image recognizing means and the target image which is stored in advance enables substantially accurate adjustment of the needle direction and position.

Preferably, the apparatus may further comprise needle ejector means for ejecting the needle from the adjuster table when it is judged that the orientation of the needle on the adjuster table is not adjustable. Thereby, the needle direction adjustment step can be further smoothly carried on.

Preferably, the needle transport means may include needle suction means with an air intake port for drawing air inside to attract the needle thereto, and transfer means for transferring the needle suction means from the adjuster table to the needle retaining means, and the air intake port of the needle suction means may be arranged at a position substantially corresponding to the position of the needle in the adjusted orientation on the adjuster table.

With this arrangement, the needle whose direction and position are adjusted by the needle orientation adjuster means is attracted to the needle suction means by an air suction force, and the needle other than the proper posture is not carried by the needle suction means. Accordingly, there can be assuredly eliminated the drawback that the needle whose orientation is not completely adjusted by the needle orientation adjuster means is erroneously carried to the needle retaining means.

BRIEF DESCRIPTION OF THE DRAWINGS

FIG. 12A is a front view of a needle swaging device in the manufacturing apparatus;

FIG. 12B is a cross sectional view of the needle swaging device taken along the line A—A in FIG. 12A.

BEST MODE FOR CARRYING OUT THE INVENTION

A preferred embodiment according to this invention is described with reference to the accompanying drawings.

Figure 1:
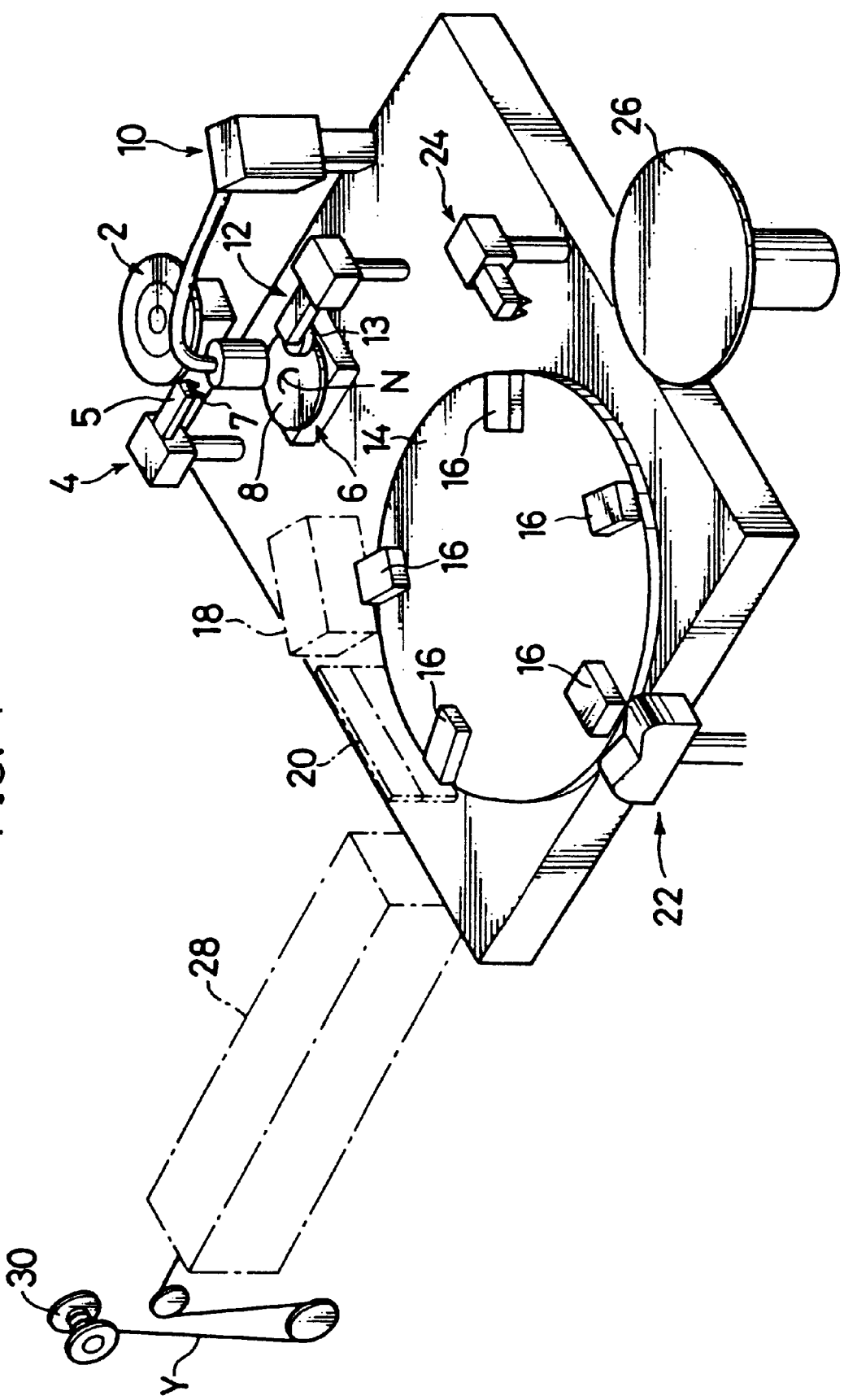
FIG. 1 is a perspective view of an entire arrangement of a needle attached suture manufacturing apparatus as an embodiment according to this invention.
Figure 2:
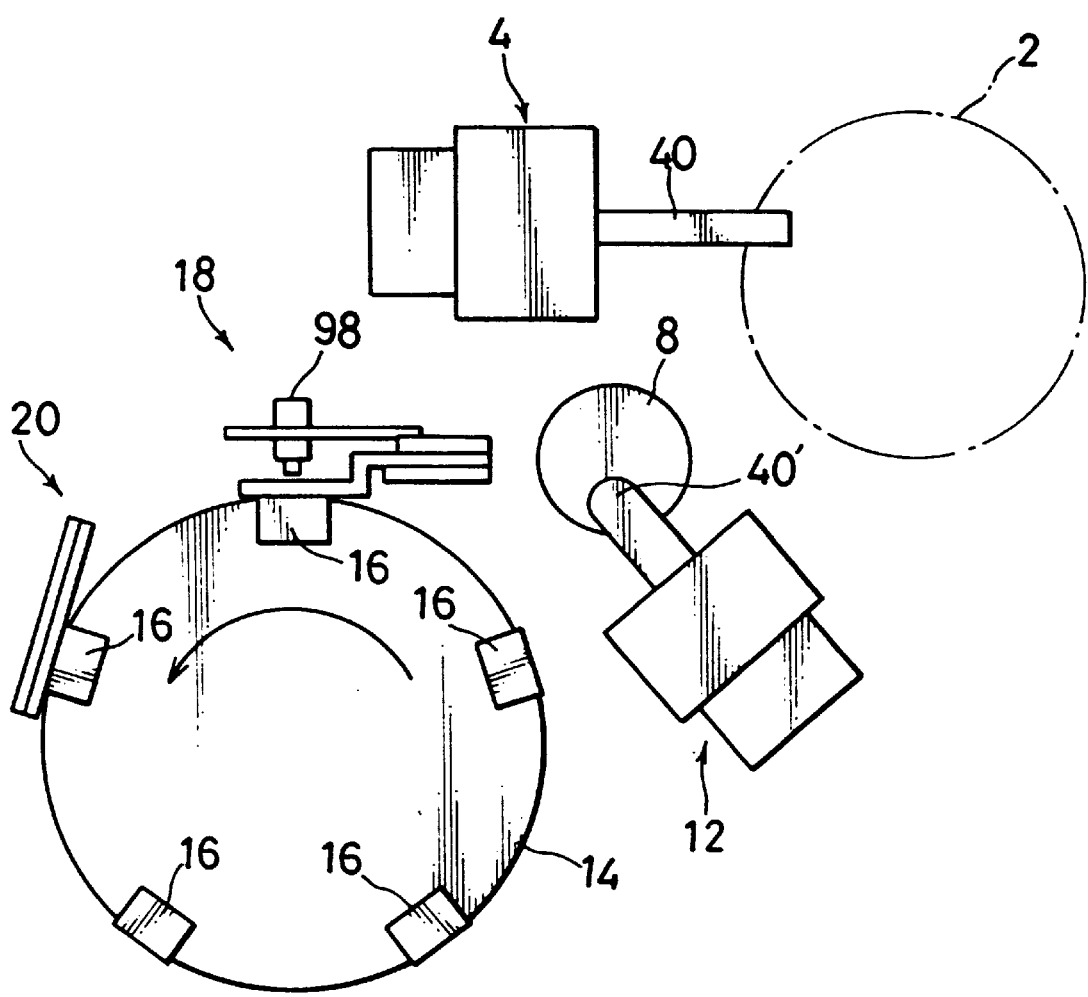
FIG. 2 is a plan view showing an essential portion of the manufacturing apparatus.

FIGS. 1 and 2 show an apparatus for manufacturing needle attached sutures embodying this invention. The apparatus comprises a needle supply device 2, a needle transport device 4, a needle orientation adjuster device 6, a needle pickup device (needle transport means) 12, a turntable (transport means) 14, a needle end adjuster device 18, a needle swaging device 20, a pull test device 22, a needle discharge device 24, a needle discharge table 26, and a suture supply device 28.

The needle transport device 4 is adapted for picking up a needle N supplied to a predetermined position on the needle supply device 2 and for transporting the same to the needle orientation adjuster device 6. Note that the needle N handled by the inventive needle attached suture manufacturing apparatus has a shape substantially curved into an arc and is formed with a suture insertion hole axially opened at the end thereof.

The needle orientation adjuster device 6 has an adjuster table 8 on which the needle N is to be placed, and an image recognizer 10 such as a CCD. As will be described later, the needle orientation adjuster device 6 is constructed such that the position and the direction of the needle N placed on the adjuster table 8 are coincident with a target position and direction as accurately as possible.

The needle pickup device 12 is adapted for picking up the needle N whose position and direction have been adjusted on the adjuster table 8 and for supplying the same to the needle retaining unit 16 on the turntable 14.

The turntable 14 is driven to make turns on a base block and to be vertically movable, and is provided with a plural needle retaining units 16 along a circumference thereof. Each needle retaining unit 16 is provided to hold the needle N supplied from the needle pickup device 12 thereon. With a rotation of the turntable 14 to a certain angular position, the needle retaining unit 16 transports the needle N to the needle end adjuster device 18, the needle swaging device 20, the pull test device 22, and the needle discharge device 24 in this order.

The needle end adjuster device 18 is adapted for adjusting the end of the needle N held by the needle retaining unit 16 which is moved to a predetermined position on the turntable 14. The needle swaging device 20 is adapted for swaging the end of the needle N from upward and downward in a state that a suture Y supplied from the suture supply device 28 is inserted in an insertion hole in the end of the needle N which is securely held on the needle retaining unit 16. Thereby, the suture Y and the needle N are combined with a predetermined pressing (swaging) force to produce a needle attached suture. The arrangement of the needle end adjuster device 18 and the needle swaging device 20 is described later in detail.

The suture supply device 28 is constructed such that the suture Y wound around a bobbin 30 is drawn out by a certain length and cut thereat to insert the suture Y of the certain length into the insertion hole at the end of the needle N which is assuredly held on the needle retaining unit 16.

The pull test device 22 is adapted for inspecting whether the combining strength of the suture Y and the needle N is sufficient by exerting the suture Y a tension force directing downward.

The needle discharge device 24 is provided with a needle gripper at the lead end of a pivotal arm. The needle gripper picks up the needle N (attached with the suture Y) on the needle retaining unit 16 and discharges the needle N onto the needle discharge table 26.

The detailed arrangement of the needle transport device 4 is described with reference to FIG. 3. The needle transport device 4 has a base member 32 on which an air cylinder 34 is provided in an upright posture. At an upper end of an expandable rod 35, there is fixedly mounted a mounting member 36. When the air cylinder 34 is driven to an expanded state and a contracted state, the mounting member 36 is moved upward and downward.

A pivot support member 37 is fixedly connected to the mounting member 36 horizontally. A pivotal shaft 38 is pivotally supported to the pivot support member 37 about a vertical pin. At a lower end of the pivotal shaft 38, there is connected a base end of a pivotal arm 40 (not shown), and at the lead end of the pivotal arm 40, there are provided a fixed claw 41A and a movable claw 41B. The movable claw 41B is slidably moved by an-air cylinder or its equivalent in a direction toward and away from the fixed claw 41A, thereby changing the state of the needle N to a gripped state in which the needle N is gripped between the fixed claw 41A and the movable claw 41B and to a released state in which the gripped state is released.

A drive motor 42 is fixedly mounted on the mounting member 36. An output shaft of the motor 42 and an upper end of the pivotal shaft 38 are connected via a belt 44. When the motor 42 is driven, the pivotal arm 40 is pivotally rotated about the axis (vertical pin) of the pivotal shaft 38. A pivotal member 46 is fixedly mounted to the pivotal shaft 38. Stoppers 47 and 48 are fixedly mounted on the upper surface of the pivot support member 37 at the left wing and the right wing relative to the pivotal member 46, respectively in the drawing. By a pivotal contact of the pivotal member 46 with the stopper 47 or 48, the moving range of the pivotal arm 40 is determined. The moving range of the pivotal arm 40 is set between a gripped position at which the needle N supplied to the predetermined position on the needle supply device 2 is enabled to be gripped between the claws 41A and 41B, and a position at which the needle N gripped by the claws 41A and 41B can be placed on the adjuster table 8.

Figure 4:
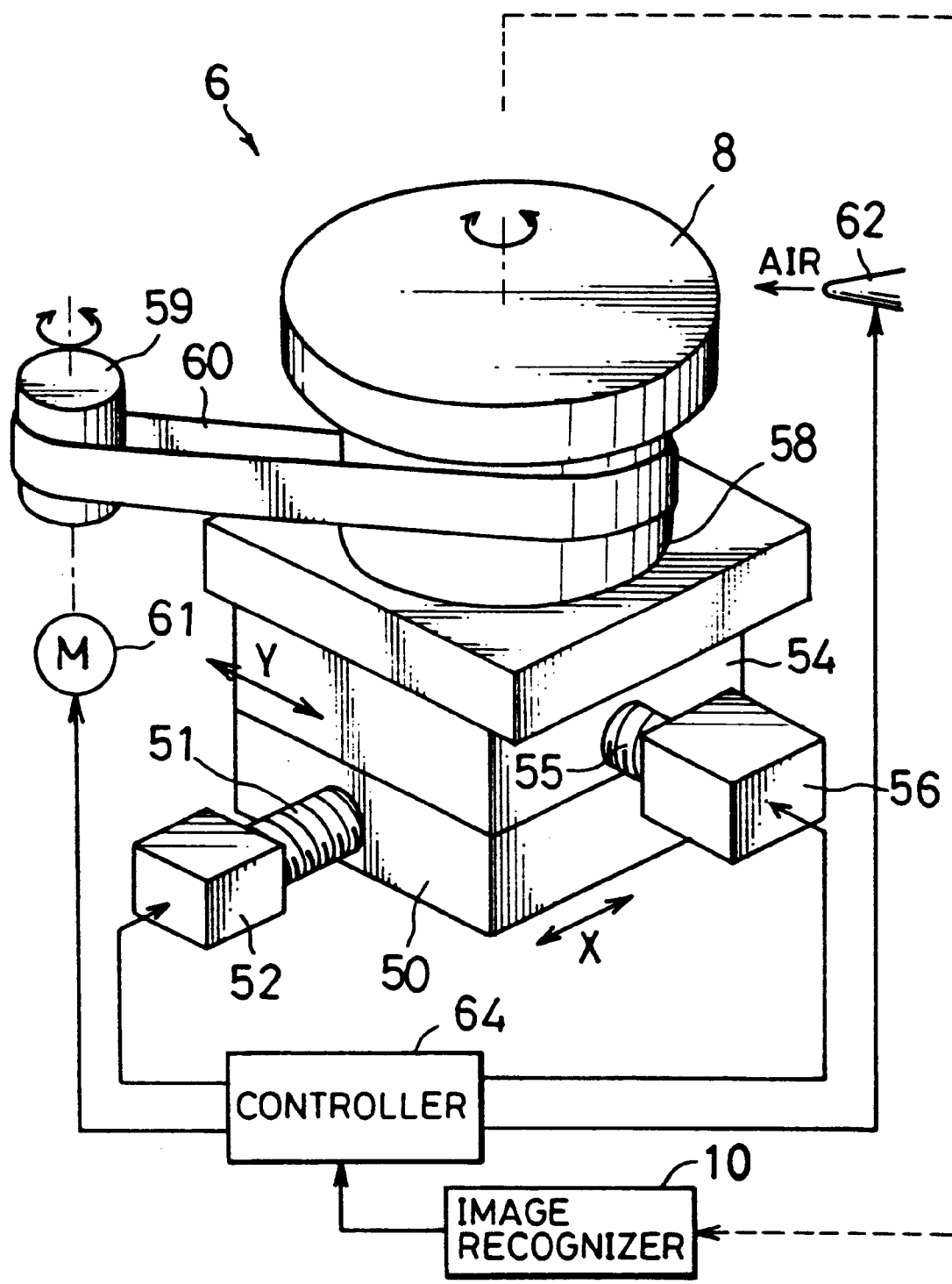
FIG. 4 is a perspective view of a needle direction adjuster device in the manufacturing apparatus.

The detailed arrangement of the needle orientation adjuster device 6 is described with reference to FIG. 4. A slide block 50 is arranged on a base block to be slidably movable in the X-direction in FIG. 4. The slide block 50 is slidable in the X-direction by a threaded screw 51 and a motor 52 which drives the threaded screw 51.

On the slide block 50, there is mounted a slide block 54 which is slidable along the Y-direction perpendicularly crossing the X-direction. The slide block 54 is slidable in the Y-direction by a threaded screw 55 and a motor 56 which drives the threaded screw 55.

A rotary shaft 58 is mounted on the slide block 54 to be rotatable about an axis thereof extending vertically. The adjuster table 8 is fixedly mounted on an upper end of the rotary shaft 58. The rotary shaft 58 is connected to a pivotal shaft 59 via a belt 60. When the pivotal shaft 59 is driven by a motor 61, the rotary shaft 58 and the adjuster table 8 are integrally rotated. Thus, the adjuster table 8 is movable in three directions driven by the motors 52, 56 and 61, respectively.

On a side of the adjuster table 8, there is mounted an air ejector nozzle 62 to eject the needle N from the adjuster table 8 by blowing high-pressured air onto the needle N placed on the adjuster table 8.

Figure 5A:
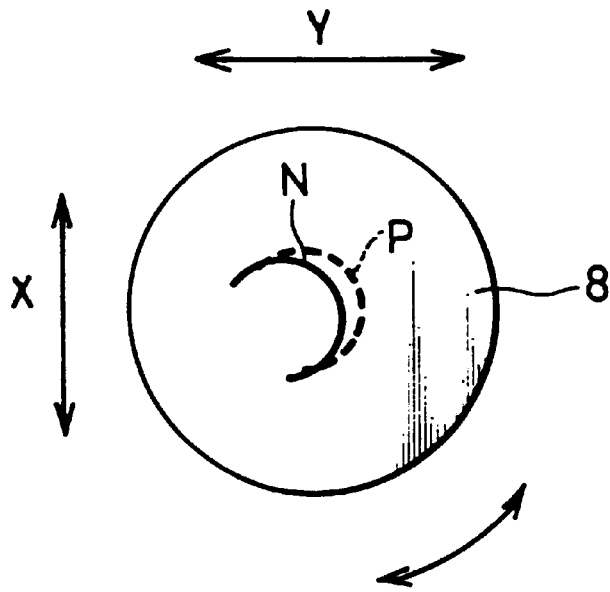
FIG. 5A is a plan view showing a state in which a direction and a position of an image of a needle recognized on an adjuster table of the needle orientation adjuster device do not coincide with those of a stored target image.
Figure 5B:
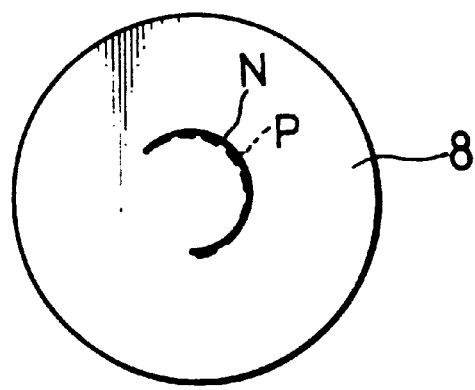
FIG. 5B is a plan view showing a state in which the direction and the position of the recognized image coincide with those of the target image.
Figure 5C:
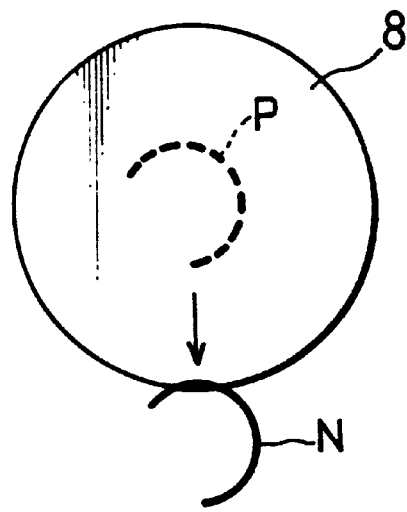
FIG. 5C is a plan view showing a state in which a needle is ejected from the adjuster table.

The image recognizer 10 recognizes an image of the needle N placed on the adjuster table 8, and outputs a signal to a controller 64 such as a computer. The controller 64 compares the orientation (direction and position) of the image of the needle N recognized by the image recognizer 10, to those of a target image P (shown by the broken line in FIG. 5A) which are stored in advance. If there is detected a difference between the recognized image and the target image, the motors 52, 54, and 61 are driven according to needs to make the recognized image coincident with the target image (as shown in FIG. 5B). If it is judged that the difference is too large to make a proper adjustment merely by moving the adjuster table 8 by the motors 52, 54 and 61, the air ejector nozzle 62 is operated to blow high-pressured air. Thereby, the needle N is ejected from the adjuster table 8 (as shown in FIG. 5C).

Figure 6:
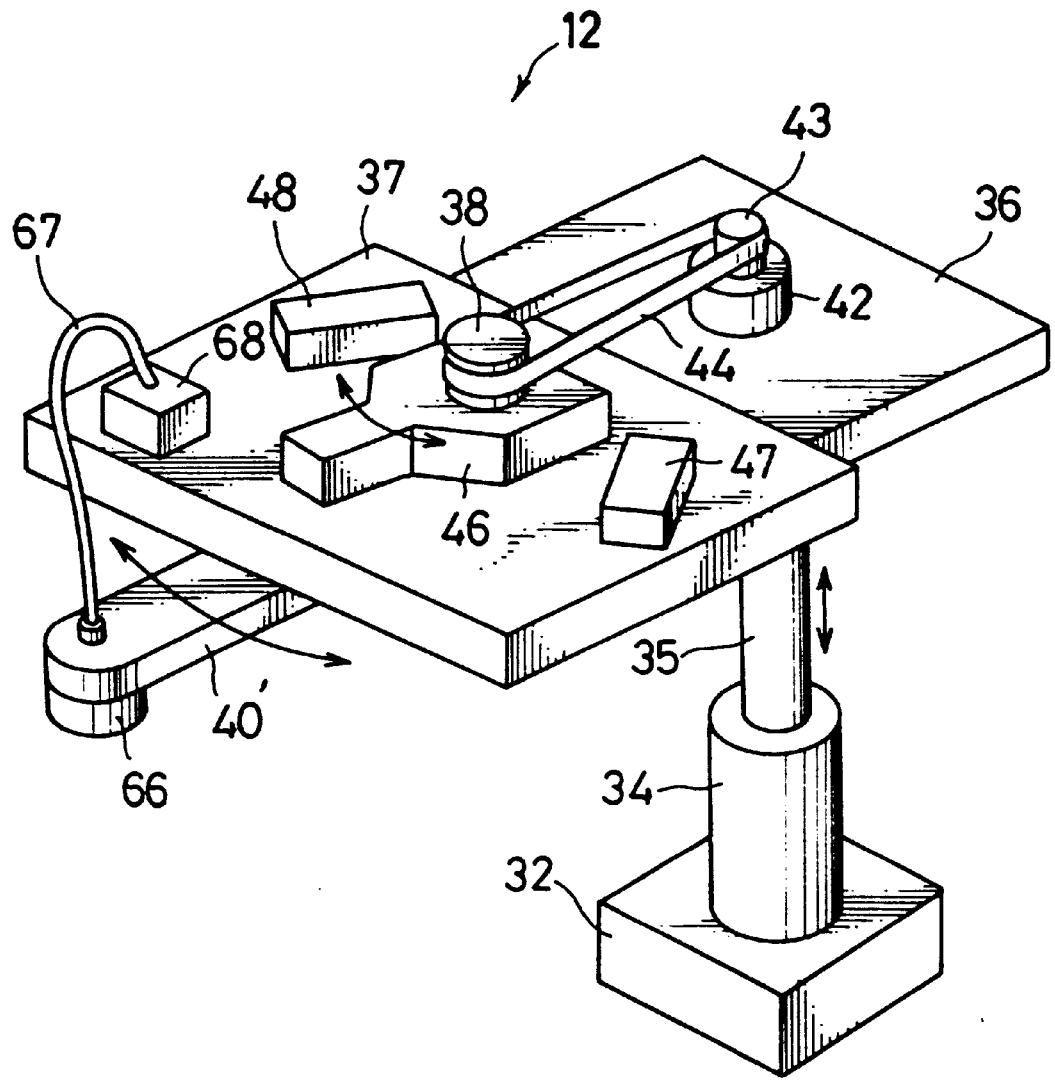
FIG. 6 is a perspective view of a needle pickup device in the manufacturing apparatus.

As shown in FIG. 6, the needle pickup device 12 has the arrangement substantially identical to that of the needle transport device 4. Similarly to the needle transport device 4, the needle pickup device 12 comprises a base block 32, an air cylinder 34, a mounting member 36, a pivot support member 37, a pivotal shaft 38, a motor 42, a belt 44, a pivotal member 46, and stoppers 47 and 48. The needle pickup device 12 is different from the needle transport device 4 in the following points.

Figure 3:
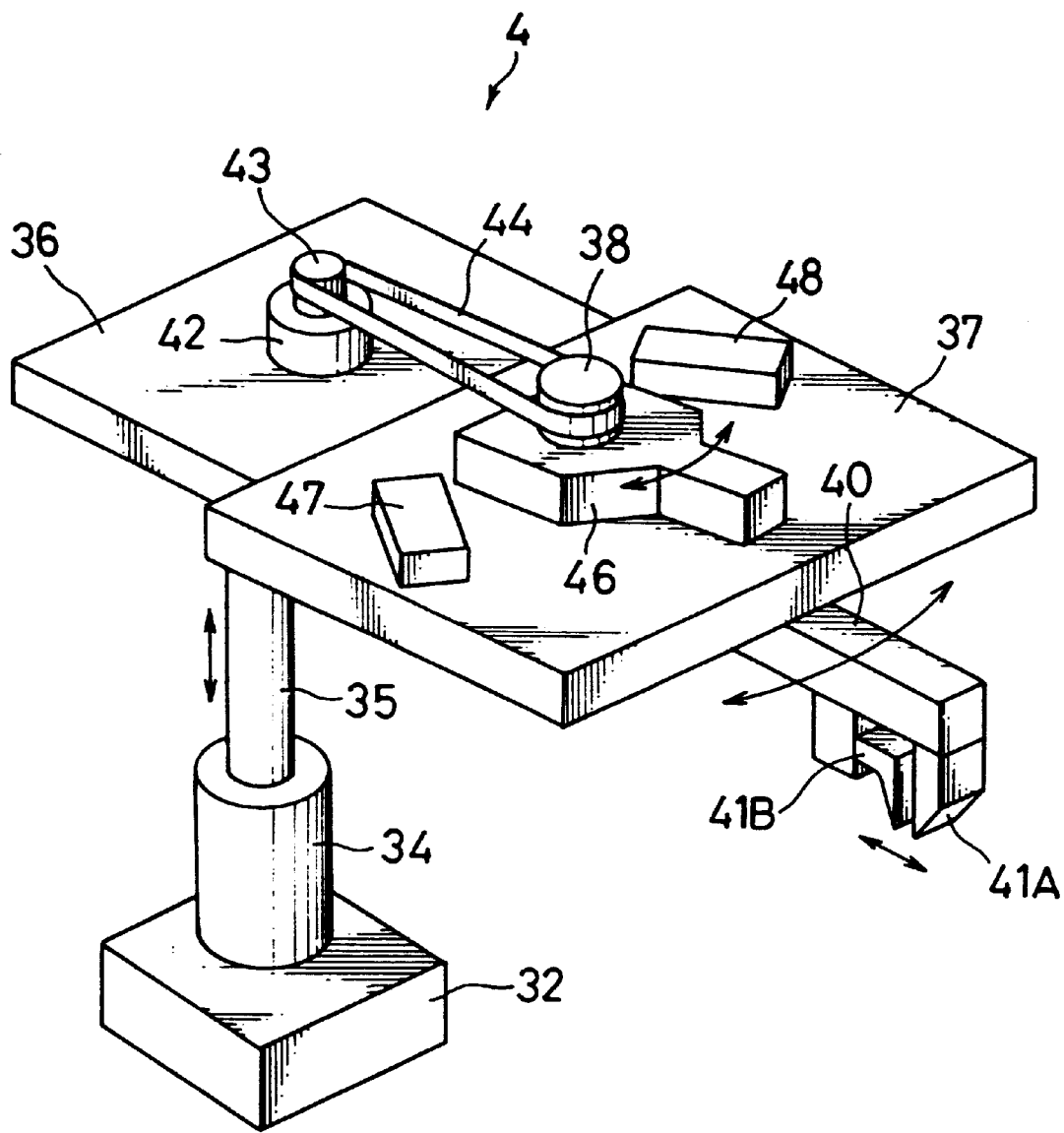
FIG. 3 is a perspective view of a needle transport device in the manufacturing apparatus.

At the lower end of the pivotal shaft 38 of the needle pickup device 12, there is fixedly mounted a base end of a pivotal arm 40" in place of the pivotal arm 40 shown in FIG. 3. At the lead end of the pivotal arm 40", there is fixedly mounted a needle suction portion 66. The moving range of the pivotal arm 40" is determined by a pivotal contact of the pivotal member 46 with the stopper 47 or 48. The moving range of the pivotal arm 40" is set between a needle receiving position at which the needle suction portion 66 is located above the adjuster table 8, and a needle transfer position at which the needle suction portion 66 is located above the needle retaining unit 16.

The needle suction portion 66 is connected to an air suction pump 68 mounted on the pivot support member 37 via an air pipe 67. When the air suction pump 68 is activated, air is sucked through a plural air intake ports 69 (see FIG. 7) formed at an underside of the needle suction portion 66. The air intake port 69 is located at such a position as to substantially correspond to the contour of the needle N whose orientation has already been adjusted on the adjuster table 8 when the needle suction portion 66 is set at the needle receiving position.

With this arrangement, the needle is transported to the needle retaining unit 16 while being attracted to the needle suction portion 66 by an air suction force in a state that the direction and position of the needle N are adjusted to those of the target image on the adjuster table 8. Contrary to this, if it is determined that the direction and the position of the needle N can not be properly adjusted, the needle suction portion 66 is not activated to carry such needle in the improper state.

The detailed arrangement of the needle retaining unit 16 is described with reference to FIG. 8. The needle retaining unit 16 each has a retainer main body 70 in the form of rectangular parallelepiped. The retainer main body 70 is fixedly mounted on the upper surface of the turntable 14 at an outer circumference.

An openable plate (openable member) 74 is rotatably mounted on the rear side of the retainer main body 70 via hinges 71 and 72. An air cylinder 76 is arranged upright at a lower side of the retainer main body 70. An expandable rod 78 of the air cylinder 76 is inserted in a through hole 77 formed in the middle of the rear side of the retainer main body 70. The through hole 77 is formed in the longitudinal direction of the air cylinder 76. When the air cylinder 76 is activated to cause the expandable rod 78 to move upward from the through hole 77, the openable plate 74 is pushed upward by the upper end of the expandable rod 78 to be set to an opened state (see the solid line in FIG. 8). When the air cylinder 76 is activated to cause the expandable rod 78 to be retracted in the through hole 77, the openable plate 74 is set to a closed state by the weight thereof (see the phantom line in FIG. 8).

Figure 8:
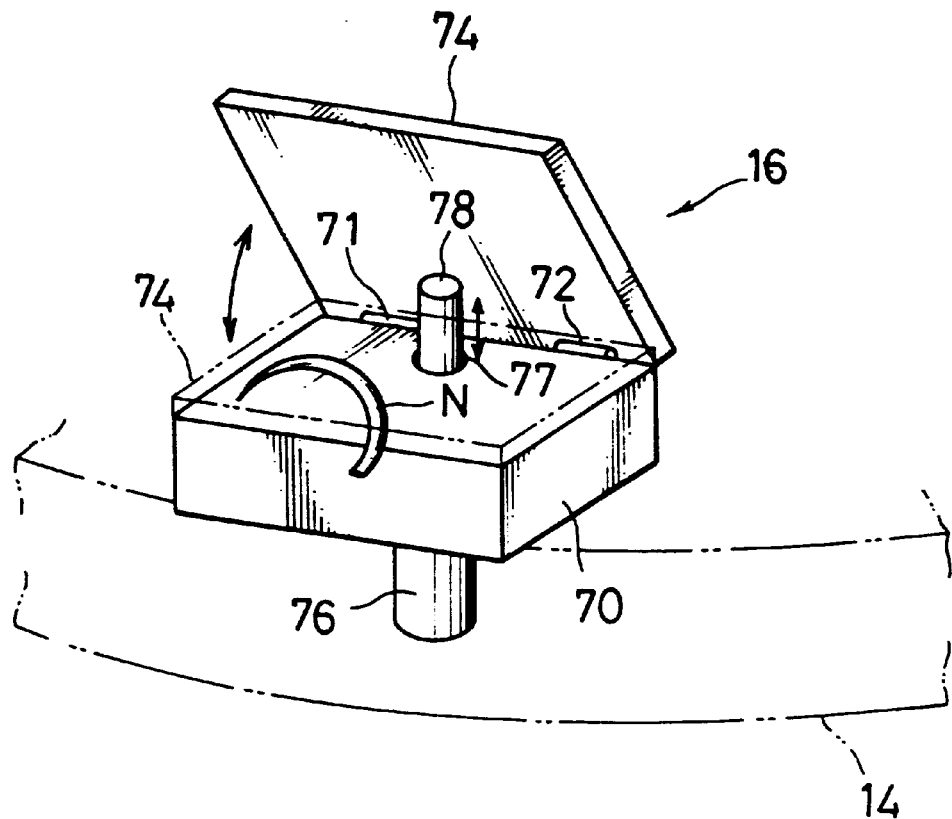
FIG. 8 is a perspective view of a needle retaining unit in the manufacturing apparatus.

When the openable plate 74 is opened up, the needle N transported by the needle pickup device 12 is placed on the upper surface of the retainer main body 70 in a state that the end of the needle N is jutted forward from the retainer main body 70 (front side in FIG. 8). Subsequently, when the openable plate 74 is closed, the needle retaining unit 16 securely holds the needle N therein with the end thereof jutted outward.

Figure 9:
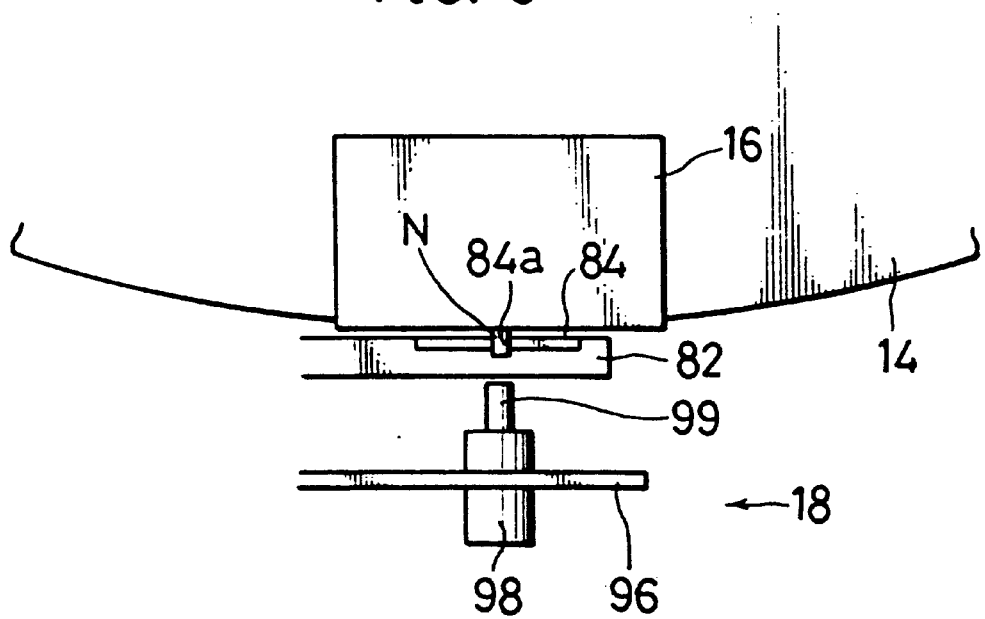
FIG. 9 is a plan view showing a positional relationship between the needle retaining unit and a needle end adjuster device.

The detailed arrangement of the needle end adjuster device 18 is described with reference to FIGS. 9 to 11.

Figure 10:
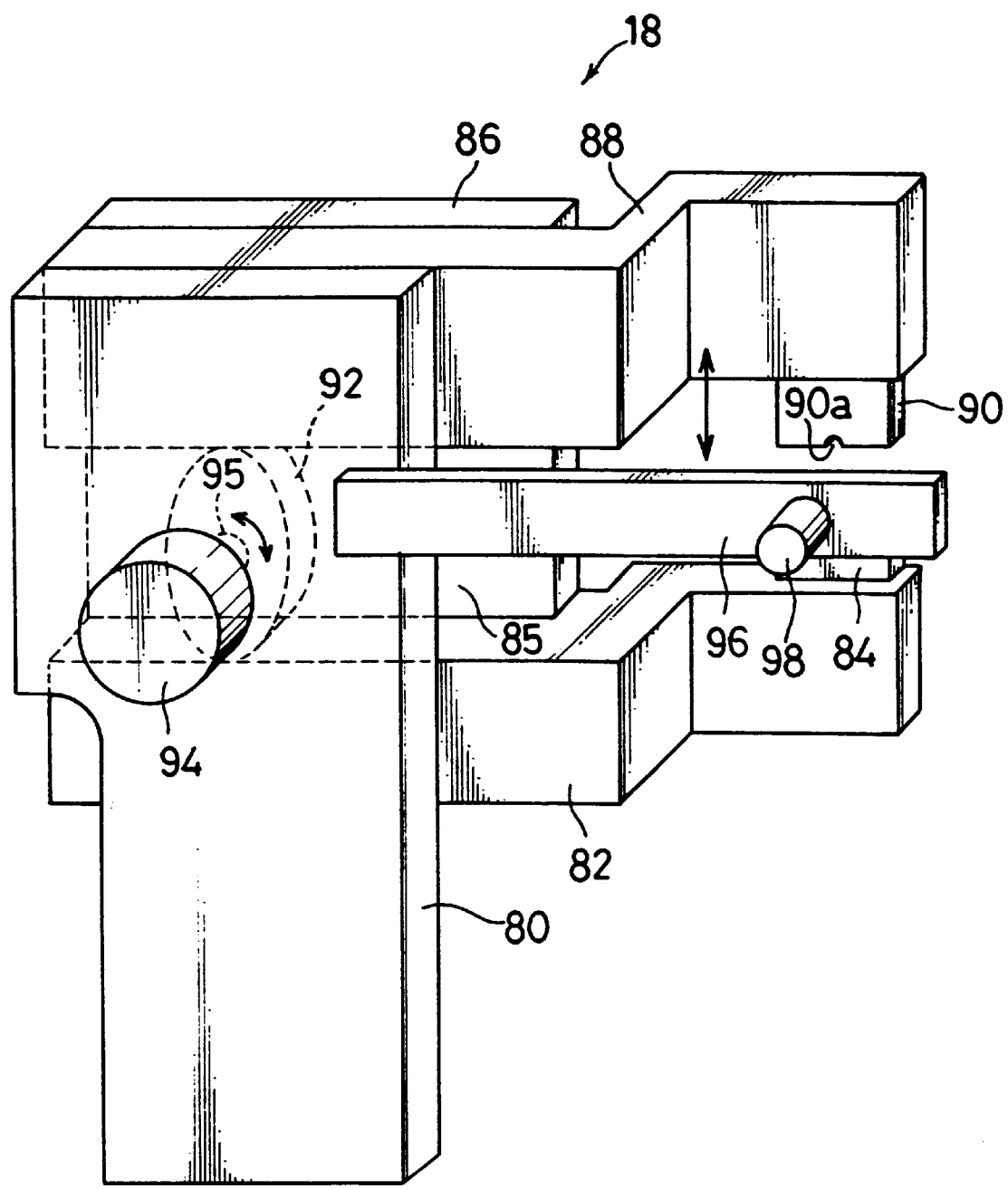
FIG. 10 is a perspective view of the needle end adjuster device.

The device 18 has a pillar (upright member) 80 in an upright posture as shown in FIG. 10. A lower gripping plate support member 82 is fixedly mounted to the pillar 80. The lower gripping plate support member 82 extends laterally along the pillar 80, and a lower gripping plate 84 is fixedly mounted in an upright posture on the upper surface of the lead end thereof. In the middle of the upper end of the lower gripping plate 84, there is formed a cutaway 84a (see FIGS. 9 and 11) in the form of a semicircular shape with a radius thereof identical to or slightly larger than the radius of the needle N.

On the upper surface of the lower gripping plate support member 82, a side wall 86 is provided as opposed to the pillar 80 with a clearance 85. An upper gripping plate support member 88 is mounted in the clearance 85 via guide means such as a rail to be vertically movable. The upper gripping plate support member 88 extends in the same direction as the lower gripping plate support member 82 from the pillar 80. An upper gripping plate 90 is fixedly mounted to the underside at the lead end of the upper gripping plate support member 88 as opposed to the lower gripping plate 84. In the middle of the lower end of the upper gripping plate 90 and just above the cutaway 84a, there is formed a cutaway 90a of a semicircular shape with a radius thereof identical to or slightly larger than the radius of the needle N.

In the clearance 85, a cam 92 is mounted rotatable between the lower gripping plate 82 and the upper gripping plate 88. The cam 92 is connected to a rotary shaft 95 of an air rotary cylinder 94 which is fixedly mounted to the pillar 80. The cam 92 is configured in such a manner as to move the upper gripping plate support member 88 upward and downward between a lowermost position at which the underside of the upper griping plate 90 comes into contact with the upper surface of the lower gripping plate 84 and an uppermost position at which the upper gripping plate 90 is vertically moved away from the lower gripping plate 84 when the cam 92 is driven by the air rotary cylinder 94.

Figure 11A:
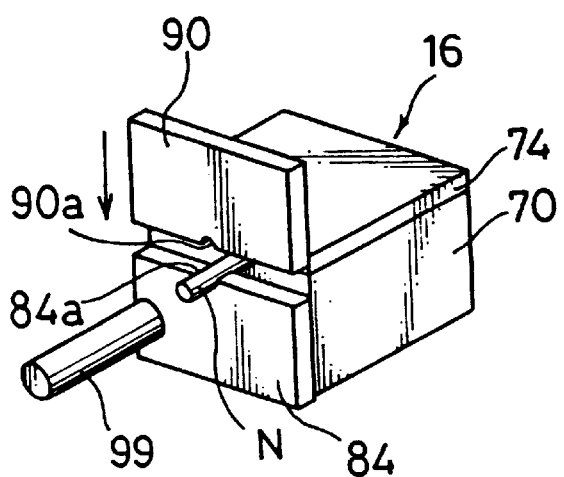
FIG. 11A is a perspective view showing a state in which an upper gripping plate is away from a lower gripping plate in the needle end adjuster device.
Figure 11B:
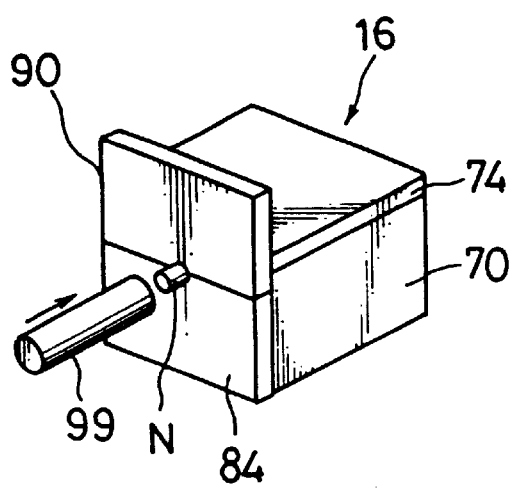
FIG. 11B is a perspective view showing a state in which the upper and lower gripping plates grip the end of the needle.

As shown in FIGS. 11A and 11B, the position of the lower gripping plate 84 and the upper gripping plate 90 is set such that the needle N held by the needle retaining unit 16 is fittingly gripped between the cutaways 84a and 90a of the lower gripping plate 84 and the upper gripping plate 90 at a portion of the blunt end except the rearmost end thereof.

Note that the target position of the needle N on the adjuster table 8 is set such that the end of the needle is jutted outward to a certain extent from the lower gripping plate 84 and the upper gripping plate 90 in a contact state of these plates 84 and 90 (i.e., in a closed state).

From the pillar 80, there extends a cylinder support member 96 in the same direction as the extending direction of the lower gripping plate support member 82 and the upper gripping plate support member 88. An air cylinder (pushing means) 98 is fixedly mounted to the lead end of the cylinder support member 96 through the cylinder support member 96 in its thickness direction. The air cylinder 98 is designed so that an expandable rod 99 is moved toward and away from the lower gripping plate 84 and the upper gripping plate 90.

Figure 11C:
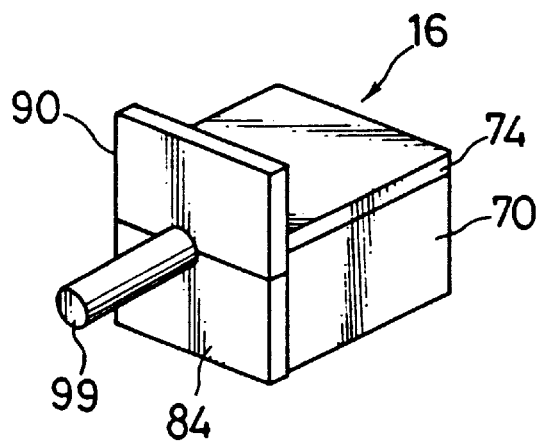
FIG. 11C is a perspective view showing a state in which the end of the needle is pushed by an expandable rod.

The expanding (extension) stroke of the air cylinder 98 is set such that when the air cylinder 88 is activated to an expanded state at the maximum level, the lead end of the expandable rod 99 pushes the end of the needle N which is fittingly interposed between the cutaways 84a and 90a, and finally comes into contact with the lower gripping plate 84 and the upper gripping plate 90 (see FIG. 11C). On the contrary, when the air cylinder 98 is activated to a contracted state, the lead end of the expandable rod 99 is away from the end of the needle N by a sufficient distance.

Figure 13:
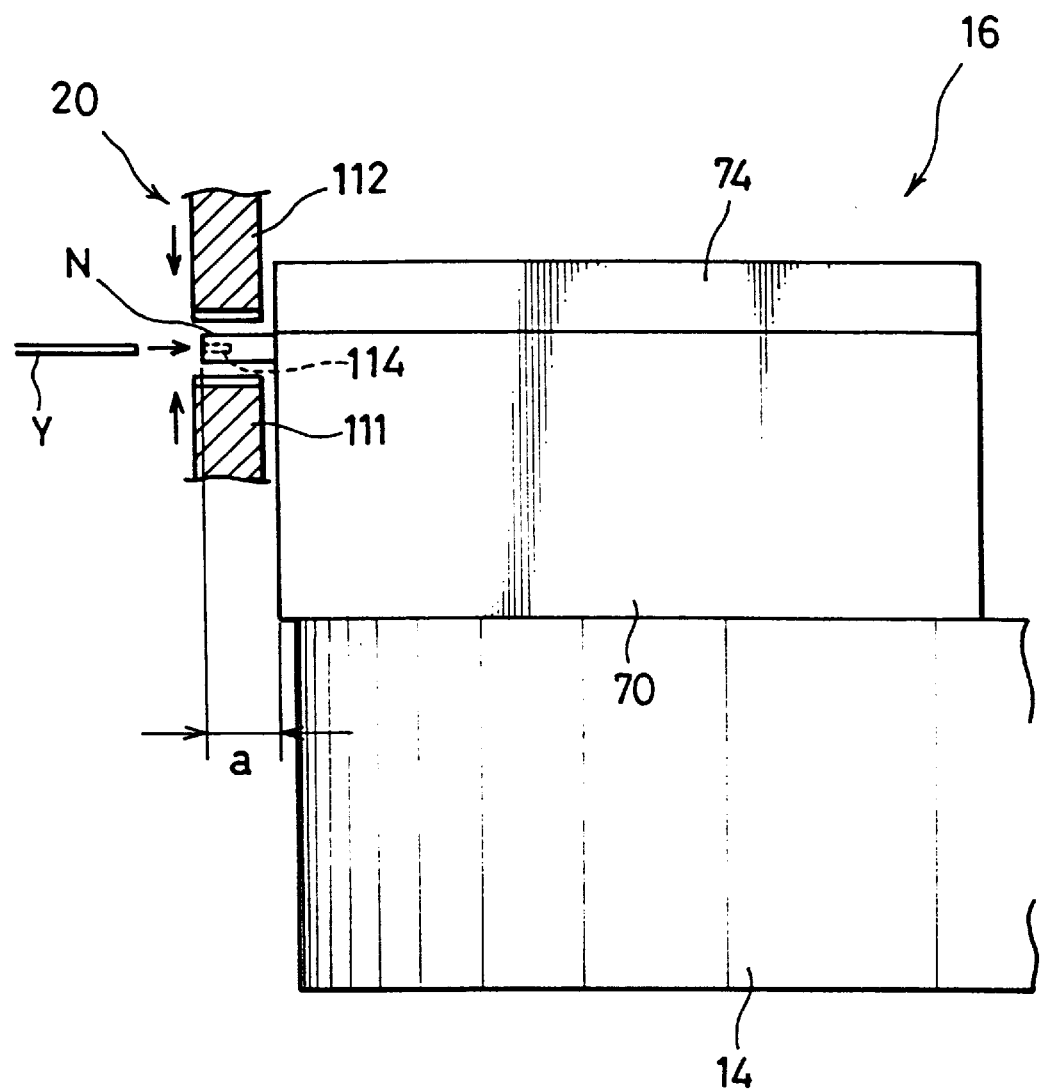
FIG. 13 is a partially cross sectional side view showing a state immediately before the end of the needle is swaged by the needle swaging device.

The detailed arrangement of the needle swaging device 20 is described with reference to FIGS. 12 and 13. The needle swaging device 20 has a horizontal pin 100 supported on a base member, a lower die support member 101 extending horizontally, and an upper die support member 102 extending horizontally. The lower die support member 101 is fixedly mounted on a base member, and is formed with a projection 101a projecting upward from the upper surface in the middle thereof with respect to the left and right direction in FIG. 12A. On the underside in the middle of the upper die support member 102 with respect to the left and right direction in FIG. 12A, there is formed a projection 102a projecting downward. The upper die support member 102 is supported rotatably about the horizontal pin 100 relative to the lower die support member 101 (i.e., set to an opened state and a closed state) in a state that the horizontal pin 100 is horizontally fitted in a hollow of the projections 101a and 102a.

The right end of the lower die support member 101 is connected to the right end of the upper die support member 102 in FIG. 12A via a tension spring 104. A cam 106 is interposed between the lower die support member 101 and the upper die support member 102 near the right ends, and is linked to an output shaft 110 of a cam drive motor 108. The cam 106 is configured such that the upper die support member 102 is pivotally rotatable about the horizontal pin 100 in accordance with a rotation of the cam 106 by the cam drive motor 108.

On the upper surface of the opposite end of the lower die support member 101 (the left end in FIG. 12A), there is arranged a lower swaging die 111 in an upright posture. An upper swaging die 112 is fixedly mounted to the underside surface at the opposite end of the upper die support member 102 as opposed to the lower swaging die 111. As shown by the solid lines inFIGs. 12A and 13, when the lower die support member 101 and the upper die support member 102 are set in a closed state, the end of the needle N held on the needle retaining unit 16 is swaged while being pressingly interposed between the lower swaging die 111 and the upper swaging die 112 in a state that the lead end of a suture Y is inserted in an insertion hole 114 formed in the end of the needle N.

An operation of the needle attached suture manufacturing apparatus according to this invention is described in the following.

The needle N is supplied to a predetermined position on the needle supply device 2, picked-up by the fixed claw 41A and the movable claw 41B of the needle transport device 4, and is transported to a predetermined position on the adjuster table 8 of the needle orientation adjuster device 6 by a pivotal rotation of the pivotal arm 40. Thereafter, the needle N is released by an operation of the claws 41a and 41B and is placed on the adjuster table 8.

The image recognizer 10 recognizes an image of the needle N placed on the adjuster table 8. The controller 64 compares the direction and the position of the recognized image, to those of the target image which are stored in advance (see FIG. 5A). The adjuster table 8 is moved in the respective directions so as to coincide the recognized image with the target image (see FIG. 5B). When it is judged that a proper adjustment is impossible, the air ejector nozzle 62 is operated to eject air, thereby ejecting the needle N from the adjuster table 8 (see FIG. 5C).

Figure 7:
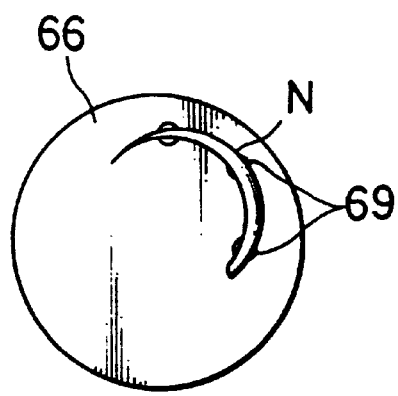
FIG. 7 is a bottom plan view of a needle suction portion of the needle pickup device.

When the direction and the position of the needle N are properly adjusted, the pivotal arm 40" of the needle pickup device 12 is moved, and the needle suction portion 66 provided at the lead end of the pivotal arm 40" is positioned above the needle N. Thereafter, when the air suction pump 68 is activated, air is sucked through the air intake ports 69. As shown in FIG. 7, the air intake port 69 is arranged at such a position as to substantially correspond to the position of the needle N when the orientation of the needle N is properly adjusted. Accordingly, the needle N whose orientation is properly adjusted is sucked to the needle suction portion 66 by an air suction force, whereas the needle whose orientation is not properly adjusted is ejected from the adjuster table 8 by the air blown onto the needle N through the air ejector nozzle 62.

Subsequently, the needle N is carried to the predetermined position on the needle retaining unit 16 on the turntable 14 by a pivotal movement of the pivotal arm 40". In the needle retaining unit 16, the air cylinder 76 is activated to allow the expandable rod 78 to push up the openable plate 74, thereby the upper surface of the retainer main body 70 is exposed outside. Then, the needle suction portion 66 is positioned at which the needle N attracted thereto is located above a predetermined position 79 corresponding to the position of the needle N shown in FIG. 8. Thereupon, the air suction operation is suspended (i.e., attraction of the needle N onto the needle suction portion 66 is ceased). Thereby, the needle N is placed on the upper surface of the retainer main body 70 exactly at the predetermined position shown in FIG. 8.

Thereafter, when the air cylinder 76 is activated to allow the expandable rod to a contracted state, the openable plate 74 is closed by the weight thereof to thereby render the needle N sandwiched between the openable plate 74 and the retainer main body 70. In this state, the turntable 14 is slightly raised, and is rotated to a specified angular position. Thereby, the needle retaining unit 16 carrying the needle N thereon is transported to the needle end adjuster device 18.

After carried to the needle end adjuster device 18, the air cylinder 98 is activated to allow the expandable rod 99 to a contracted state. At this time, the upper gripping plate 90 is spaced away above the lower gripping plate 84 by a certain distance (clearance). Accordingly, the end of the needle N is carried in the clearance defined between the lower gripping plate 84 and the upper gripping plate 90. Thereafter, the turntable 14 as a whole is slightly lowered, thereby fittingly mounting the end of the needle N onto the cutaway 84a of the lower gripping plate 84 to set the needle N to a state shown in FIG. 11A.

Then, the air rotary cylinder 94 is activated to rotate the cam 92. Thereby, the upper gripping plate support member 90 is lowered integrally with the lower gripping plate 84, and thus, as shown in FIG. 11B, the end of the needle N is gripped between the cutaways 84a and 90a of the lower gripping plate 84 and the upper gripping plate 90.

Figure 11D:
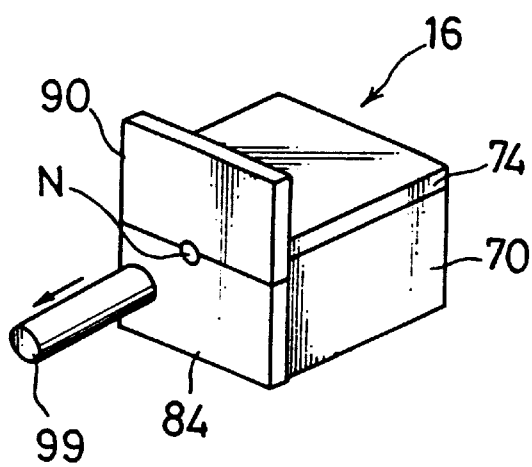
FIG. 11D is a perspective view showing a state in which the expandable rod is retracted after a pushing operation.

Subsequently, when the air cylinder 98 is activated, the expandable rod 99 is expanded to render the lead end thereof in contact with the front surface of the lower gripping plate 84 and the upper gripping plate 90 (see FIG. 11C). At this time, the expandable rod 99 pushes the end of the needle N accurately to the position flush with the front surface of the lower gripping plate 84 and the upper gripping plate 90. Thereafter, as shown in FIG. 11D, the expandable rod 99 is retracted, and the upper gripping plate 90 is raised upward. Next, the turntable 14 is raised slightly upward, and is rotated by a certain amount to move to a specified angular position. Thereby, the needle retaining unit 16 carrying the needle N is transported to the needle swaging device 20 arranged in the next step.

When being carried to the needle swaging device 20, as shown by the phantom line in FIG. 12A, the upper swaging die 112 is away above the lower swaging die 111 by a certain distance (clearance). Then, the turntable 14 is angularly displaced to transport the end of the needle N to a specified position between the lower swaging die 111 and the upper swaging die 112. Thereupon, the turntable 14 is lowered to render the upper end of the lower swaging die 111 in contact therewith.

The suture Y is supplied from the suture supply device 28, and the lead end of the suture Y is inserted into the insertion hole 114 at the end of the needle N. In this state, the cam 106 is rotated to lower the upper swaging die 112, thereby allowing the end of the needle N to be swaged between the upper swaging die 112 and the lower swaging die 111. Thus, the end of the needle N is swaged by the needle swaging device 20, and the lead end of the suture Y is fixedly attached to the end of the needle N.

At this time, an amount a of the needle N jutting out from the needle retaining unit 16 (see FIG. 13) is accurately adjusted by the needle end adjuster device 18. Accordingly, the lower swaging die 111 and the upper swaging die 112 accurately position the needle N including the swaged portion. Thereby, a desired swaging strength (combining strength of the needle N with the suture Y) is obtainable.

After the swaging operation is completed, the upper swaging die 112 is raised up, and the turntable 14 is raised by a small amount and then rotated to a certain angular position. Thereby, the needle N is transported to the pull test device 22 to inspect whether the swaging strength is sufficient. The needle N which passes the inspection by the pull test device 22 is carried to the needle discharge device 24 while being carried on the needle retaining unit 16 by a further rotation of the turntable 14, and then is discharged onto the needle discharge table 26 by the needle discharge device 24.

The present invention is not limited to the above embodiment and may take the following modifications and alterations.

(1) The needle retaining unit 16 may be fixedly mounted at a certain position, and the needle end adjuster device 18 and the needle swaging device 20 may be selectively transported to the needle retaining unit 16. In this case, however, a transportation facility of a large scale is required. Accordingly, the movable needle retaining unit 16 is advantageous in view of simplification of the facility and in smooth transportation of needle from the needle end adjusting step to the swaging step.

Transport means for transporting the needle retaining unit 16 is not limited to the arrangement of the turntable 14. The needle retaining unit 16 may be transported by a belt conveyor, for example. However, the arrangement in which the plural needle retaining units 16 are arranged along the circumference on the turntable 14 is advantageous in efficient production of needle attached sutures because all the needle retaining units 16 are fully operable without time loss.

(2) In the case where the needle retaining unit can assuredly hold the needle N, the gripping means may be omitted. However, the arrangement shown in the above embodiment in which the end of the needle N is gripped between the gripping plates 84 and 90, and the expandable rod 99 (pushing means) is moved forward to the position in contact with the front surface of the gripping plates 84 and 90 is advantageous in the following point. That is, even if the moving stroke of the expandable rod 99 is varied to a certain range, this arrangement enables the end position of the needle N to be flush with the front surface of the gripping plates 84 and 90.

(3) There may be formed a needle fitting recess in the surface of the retainer main body 70 opposing to the openable member to fittingly place the needle therein in a certain orientation. The provision of the needle fitting recess substantially corresponding to the contour of the needle is advantageous in restricting the displacement of the needle N which is held in the retainer main body 70 only in the direction along the axis thereof, thereby reliably eliminating the possibility that the needle N is deflected in a direction other than the direction along the axis thereof (i.e., rightward or leftward direction).

(4) In the foregoing embodiment, the pushing means is the expandable air cylinder 98. However, other expander means such as a hydraulic cylinder and a solenoid may be applicable.

(5) In the case where the needle supply device 2 of the apparatus shown in FIG. 1 is capable of assuredly supplying a needle N to a predetermined position in a state that the orientation (direction and position) of the needle N is adjusted, the needle orientation adjuster device 6 may be omitted, and the needle N may be transported directly from the needle supple device 2 to the needle retaining unit 16.

Further, even in the case where the needle orientation adjuster device 6 is used, the arrangement of the needle transport means (in the above embodiment, the needle pickup device 12) for transporting the needle N from the needle orientation adjuster device 6 to the needle retaining unit 16 is not limited to the one shown in the embodiment. For example, the arrangement similar to the needle transport device 4 (i.e., gripping type) may be applicable.

(6) In the case where various kinds of needles whose curvature is varied are to be used, different types of needle suction portions each provided with an air intake port at a position corresponding to the configuration of the needle may be prepared, and the suitable needle suction portion 66 may be detachably attached to the lead end of the pivotal arm according to needs. This arrangement is advantageous in conducting a needle pickup operation by the needle suction portion with high efficiency.

(7) The arrangement of the gripping means for gripping the needle N in the needle end adjuster device 18 is not limited to any specific one. For example, the lower support member 82 and the upper support member 88 may be linked by a tension spring similar to the one used in the needle swaging device 20, and may be supported rotatably about a horizontal pin (i.e., set to an opened state and a closed state), similar to the arrangement of the linkage between the lower die support member 101 and the upper die support member 102.

(8) In the above embodiment, the openable member 74 is connected to the retainer main body 70 via hinges.

Alternatively, the connection may be performed using various kinds of spring.

(9) In the aforementioned embodiment, the drive means for moving the pivotal arm 40 of the needle transport device 4 and the pivotal arm 40" of the needle pickup device 12 are a rotary drive motor mounted with a belt. Alternatively, other drive means such as air rotary cylinder may be used.

EXPLOITATION IN INDUSTRY

As mentioned above, the present invention is effectively applicable, in the field of producing sutures attached with needles for surgical operations, to a method for combining the lead end of the suture with the end of the needle and an apparatus therefor.

We claim:

1. A method for manufacturing a needle attached suture in which a suture is combined with a needle by swaging an end of the needle with the suture being inserted in an insertion hole formed in the end of the needle, while retaining the needle with the end thereof exposed outside, the method comprising the steps of:

(a) retaining the needle in such a manner that the needle is displaceable in a direction along an axis of the end thereof;

(b) positioning the end of the needle in a position for swaging by pushing the end of the needle; and (c) swaging the end of the needle with the suture.

2. An apparatus for manufacturing a needle attached suture comprising:

needle retaining means for retaining a needle with an end thereof exposed outside such that the needle retained by the needle retaining means is displaceable in a direction along an axis of the end of the needle;

swaging means for swaging the end of the needle with a suture being inserted in an insertion hole formed in the end of the needle to combine the suture with the needle; and pushing means for pushing the end of the needle to a predetermined target swaginq position relative to the needle retaining means to render the end position of the needle coincident with the target swaging position.

3. The apparatus according to claim 2, further comprising transport means for transporting the needle retaining means, from a position at which the end is pushed by the pushing means to such a position as to allow the end of the needle to be swaged by the swaging means, the pushing means being arranged at a position different from the swaging means.

4. The apparatus according to claim 3, wherein the transport means includes a turntable operable to rotate, and the turntable is arranged with a plural needle retaining means along an outer circumference thereof.

5. The apparatus according to claim 2, further comprising gripping means arranged between the needle retaining means and the pushing means for restricting a certain end portion of the needle except a rearmost end thereof from moving in a direction different from the pushing direction of the pushing means.

6. The apparatus according to claim 5, wherein the gripping means includes a gripping plate for fixedly gripping the end of the needle, and the pushing means pushes the end of the needle to such a position as to render the pushing means in contact with a surface of the gripping plate opposing to the pushing means.

7. The apparatus according to claim 3, wherein the needle retaining means includes a retainer main body carried by the transport means, an openable member linked to the retainer main body to be openable with respect to the retainer main body, and drive means for setting the openable member to an opened state and a closed state, the needle being held by the retainer main body and the openable member in the closed state.

8. The apparatus according to claim 2, wherein the pushing means includes an expandable member, and the expandable member is so arranged as to allow a lead end thereof to push the end of the needle to a predetermined position when the expandable member is set to an expanded state.

9. The apparatus according to claim 2, further comprising needle orientation adjuster means for rendering an orientation of the needle coincident with a predetermined target orientation, and needle transport means for transporting the needle in the orientation thereof adjusted by the needle orientation adjuster means to the needle retaining means.

10. The apparatus according to claim 9, wherein the needle orientation adjuster means includes an adjuster table horizontally movable and rotatable about an axis thereof for placing the needle thereon, table drive means for moving the adjuster table to a desired direction, image recognizing means for recognizing an image of the needle placed on the adjuster table, and drive control means for controlling the table drive means to render a position of the image of the needle recognized by the image recognizing means coincident with a target image position.

11. The apparatus according to claim 10, further comprising needle ejector means for ejecting the,needle from the adjuster table when it is judged that an orientation of the needle on the adjuster table is not adjustable.

12. The apparatus according to claim 9, wherein the needle transport means includes needle suction means with an air intake port for drawing air inside to attract the needle thereto, and transfer means for transferring the needle suction means from the adjuster table to the needle retaining means, the air intake port of the needle suction means being arranged at a position substantially corresponding to the position of the needle in the adjusted orientation on the adjuster table.

* * * * *